United States Patent [19]
Saville et al.

[11] Patent Number: 4,816,328
[45] Date of Patent: Mar. 28, 1989

[54] BREATHABLE, NON-LINTING LAMINATE

[75] Inventors: Mark K. Saville, Newark, Del.; William J. Gorak, Jr., Elkton, Md.; Ronald L. Bove, Newark, Del.

[73] Assignee: W. L. Gore & Associates, Inc., Newark, Del.

[21] Appl. No.: 120,330

[22] Filed: Nov. 13, 1987

[51] Int. Cl.$^4$ .................. B01D 39/08; B01D 39/16; B32B 27/12
[52] U.S. Cl. .................. 428/246; 55/486; 55/487; 55/524; 55/528; 428/251; 428/252; 428/285; 428/286; 428/287; 428/311.5; 428/316.6; 428/317.5; 428/317.7; 428/422; 428/922
[58] Field of Search .......... 55/486, 487, 524, 528; 428/246, 251, 252, 285, 286, 287, 311.5, 316.6, 317.5, 317.7, 422, 922

[56] References Cited

U.S. PATENT DOCUMENTS

| 4,025,679 | 5/1977 | Denny | 55/527 |
| 4,187,390 | 2/1980 | Gore | 55/486 |
| 4,194,041 | 3/1980 | Gore et al. | 428/316.6 |
| 4,324,574 | 4/1982 | Fagan | 55/524 |
| 4,361,619 | 11/1982 | Forsten et al. | 55/528 |
| 4,370,376 | 1/1983 | Gangal et al. | 55/524 |
| 4,522,876 | 6/1985 | Hiers | 55/528 |
| 4,532,316 | 7/1985 | Henn | 528/59 |
| 4,539,021 | 9/1985 | Hager et al. | 55/524 |
| 4,582,747 | 4/1986 | Hirakawa et al. | 428/311.5 |
| 4,612,237 | 9/1986 | Frankenberg | 55/528 |

Primary Examiner—James C. Cannon
Attorney, Agent, or Firm—Mortenson & Uebler

[57] ABSTRACT

A flexible, breathable, antistatic, non-flammable, filtering, non-linting, clean and cleanable composite laminate is provided. The laminate comprises a middle layer of a non-flammable fabric, preferably a polyamide or glass fabric, containing an antistatic agent, and a top and bottom layer each containing a sheet of porous, expanded polytetrafluoroethylene bonded to the middle layer by means of an adhesive between the middle layer and the top and bottom layers. Preferably the top and bottom layers comprise (a) a flexible, first layer of hydrophobic material having a moisture vapor transmission rate exceeding 1000 gms./m$^2$·day and an advancing water contact angle exceeding 90 degrees; and (b) a continuous hydrophilic layer attached to the first layer, the hydrophilic layer having a moisture vapor transmission rate exceeding 1000 gms./m$^2$·day and forming a barrier to passage of fluids with low surface tension, wherein the hydrophobic layers are both external to the middle layer. The laminate is useful as a cover for cleaned aerospace equipment during retrofitting, shipping and storage.

11 Claims, 1 Drawing Sheet

BREATHABLE, NON-LINTING LAMINATE

BACKGROUND OF THE INVENTION

This invention relates to a composite laminate useful, inter alia, as a covering for cleaned aerospace equipment which will keep such equipment absolutely clean during retrofitting, shipping and storage.

For covering such equipment, a clean and cleanable product is required which is non-linting and which is a very effective particle filter. The material must be sewable or joinable, it must dissipate electrical charges, and it must be non-combustible.

Aerospace equipment, especially equipment associated with shuttle and rocket flights, is assembled and/or cleaned in clean areas. Once cleaned, it is important to keep such equipment clean prior to and during use.

Equipment for use on shuttle flights needs to be kept free of all dust, dirt and organic vapors. During retrofitting of the shuttle between flights, major pieces of equipment, e.g., the cargo doors, require such protection.

Heretofore, "Chemstat 919", a monofilament polyamide fabric sold under the trademark Nomex®, and having interwoven conducting thread, has been used, but this material is a poor particulate filter and can allow submicron particles through onto the equipment to be protected. Also, "Herculite", a plasticized PVC coating on nylon fabric has been used for clean area barriers, but it can give off a plasticizer as a gas which can fog lenses.

Until now, there has been no entirely satisfactory covering material for such sensitive equipment.

As used herein, the term "porous, expanded polytetrafluoroethylene" is as disclosed in U.S. Pat. No. 3,953,566. The term "breathable" is as disclosed in U.S. Pat. No. 4,194,041. Both of these patents are assigned to assignee herein and both are incorporated here by reference thereto.

SUMMARY OF THE INVENTION

A flexible, breathable, antistatic, non-flammable, filtering, non-linting, clean and cleanable composite laminate is provided comprising a middle layer of a non-flammable fabric containing an antistatic agent, and a top and bottom layer each containing a sheet of porous, expanded polytetrafluoroethylene, the top and bottom layers being bonded to the middle layer by means of an adhesive between the middle layer and the top and bottom layers, wherein the porous, expanded polytetrafluoroethylene sheets form the external surfaces of the composite laminate. The top and bottom layer each preferably comprise a flexible, first layer of hydrophobic material having a moisture vapor transmission rate exceeding 1000 gms./m$^2$ · day and an advancing water contact angle exceeding 90 degrees, and a continuous hydrophilic layer attached to the first layer, the hydrophilic layer having a moisture vapor transmission rate exceeding 1000 gms./m$^2$ · day and forming a barrier to liquids with low surface tension. The middle layer may be a polyamide or polybenzimidazole fabric, woven, knitted or non-woven. The middle layer may alternatively be a glass cloth, glass mat or any fabric of non-flammable organic or inorganic fiber. Cationic, non-ionic or anionicantistatic agents may be used. Static electricity can also be dissipated with an electrically conducting filament incorporated in the fabric. The adhesive may be a reactive polyurethane prepolymer comprising the reaction product of (i) a polyol (A) having a number average molecular weight of from 600 to 3500 and having a functionality of at least 2; (ii) an isocyanate (B) having a functionality of at least 2; and (iii) a low molecular weight chain extender (C) having a molecular weight lower than 500 and having a functionality of at least 2, wherein the reactants are employed in such proportions so as to satisfy the following equations:

(a) $\dfrac{Eq_{NCO}}{Eq_{OH} + Eq_{CE}} \geq 1.1$ (b) $Eq_{OH} \geq Eq_{CE}$ (c) $Eq_{CE} > 0$, wherein $Eq_{NCO}$ denotes the equivalents of the isocyanate species employed, and $Eq_{OH}$ and $Eq_{CE}$ denote the respective molar equivalents of the polyol and chain extender employed, characterized in that the reactants are selected such that the reaction product of the isocyanate and chain extender provides suitable hard segments and soft segments and wherein the suitable hard segments are thermodynamically incompatible with the soft segments, the latter provided by the polyol, whereby phase separation of hard and soft segments in the prepolymer occurs at room temperature and renders the prepolymer a 100% solids, storage stable, segmented polyurethane prepolymer being an opaque solid at room temperature, the prepolymer having storage stability exceeding one month and being melt processible at room temperature below what would be considered to be the hard melt temperature.

DETAILED DESCRIPTION OF THE INVENTION AND PREFERRED EMBODIMENTS WITH REFERENCE TO THE DRAWINGS

A flexible, breathable, antistatic, non-flammable, filtering, non-linting, clean and cleanable composite laminate is provided. The laminate comprises a middle layer of a non-flammable fabric, preferably a polyamide or glass fabric, containing an antistatic agent, and a top and bottom layer each containing a sheet of porous, expanded polytetrafluoroethylene bonded to the middle layer by means of an adhesive between the middle layer and the top and bottom layers. Preferably the top and bottom layers comprise (a) a flexible, first layer of hydrophobic material having a moisture vapor transmission rate exceeding 1000 gms./m$^2$ · day and an advancing water contact angle exceeding 90 degrees, and (b) a continuous hydrophilic layer attached to the first layer, the hydrophilic layer having a moisture vapor transmission rate exceeding 1000 gms./m$^2$ · day and forming a barrier to passage of liquids with low surface tension, wherein the hydrophobic layers are both external to the middle layer. The laminate is useful as a cover for cleaned aerospace equipment during retrofitting, shipping and storage.

Figure 1:
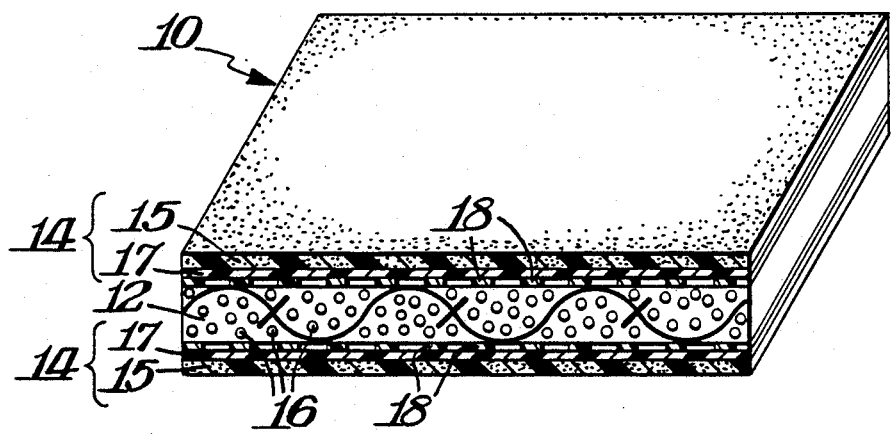
FIG. 1 is a perspective view, partly in cross section, of the composite laminate according to the invention.

A detailed description of the invention and preferred embodiments is best provided with reference to the drawings wherein FIG. 1 is a perspective view, partly in cross section, of the composite laminate 10 of the invention. Laminate 10 includes middle layer 12 of a non-flammable fabric containing an antistatic agent 16. The middle layer 12 preferably is a non-flammable polyamide, woven, knitted or non-woven, marketed by DuPont under the trademark Nomex ®. The middle layer 12 may be glass, in either cloth or mat form. An antistatic agent which is suitable is Zelec ® DP, marketed by DuPont, and described to be a dispersion of complex cationic polymers. Bonded to each side of middle layer 12 is a layer 14 containing a sheet 15 of expanded, porous polytetrafluoroethylene. Layers 14 are bonded to layer 12 by means of an adhesive 18 as shown between the middle layer 12 and the top and bottom layers 14. Layers 14 as shown comprise the porous hydrophobic layer 15 and the breathable hydrophilic layers 17 as disclosed in U.S. Pat. No. 4,194,041, and this is preferred for certain uses. However, the porous, expanded polytetrafluoroethylene layers 15 may be bonded directly to the middle layer 12 by adhesive 18. In all cases, the expanded, porous polytetrafluoroethylene layer forms the external surfaces of the composite laminate 10. Adhesive 18 is preferably the material disclosed in U.S. Pat. No. 4,532,316, namely, a reactive polyurethane prepolymer comprising the reaction product of (i) a polyol (A) having a number average molecular weight of from 600 to 3500 and having a functionality of at least 2; (ii) an isocyanate (B) having a functionality of at least 2; and (iii) a low molecular weight chain extender (C) having a molecular weight lower than 500 and having a functionality of at least 2, wherein the reactants are employed in such proportions so as to satisfy the following equations:

(a) $\frac{Eq_{NCO}}{Eq_{OH} + Eq_{CE}} \geq 1.1$ (b) $Eq_{OH} \geq Eq_{CE}$ (c) $Eq_{CE} > 0$, wherein $Eq_{NCO}$ denotes the equivalents of the isocyanate species employed, and $Eq_{OH}$ and $Eq_{CE}$ denote the respective molar equivalents of the polyol and chain extender employed, characterized in that the reactants are selected such that the reaction product of the isocyanate and chain extender provides suitable hard segments and soft segments and wherein the suitable hard segments are thermodynamically incompatible with the soft segments, the latter provided by the polyol, whereby phase separation of hard and soft segments in the prepolymer occurs at room temperature and renders the prepolymer a 100% solids, storage stable, segmented polyurethane prepolymer being an opaque solid at room temperature, the prepolymer having storage stability exceeding one month and being melt processible at room temperature below what would be considered to be the hard segment melt temperature.

Figure 2:
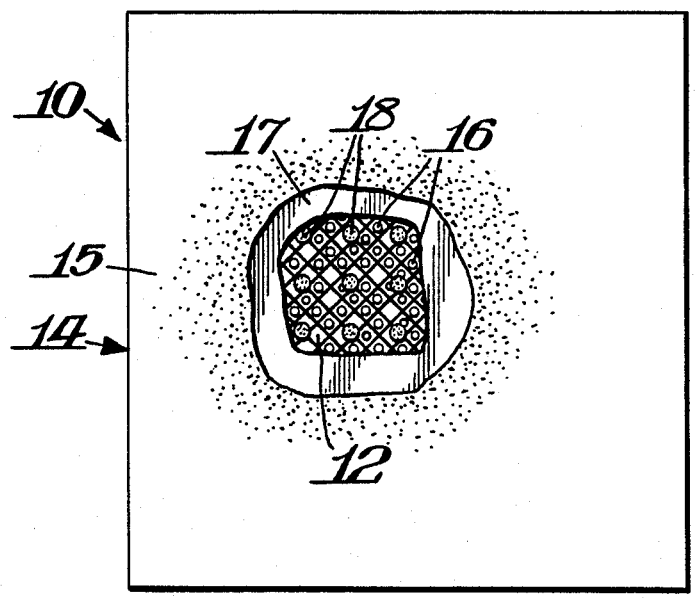
FIG. 2 is a top plan view, partly broken away, of the composite laminate of the invention.

FIG. 2 shows a top plan view of the composite laminate 10 of the invention partially broken away. Therein, middle layer 12 contains antistatic agent 16 therein and is bonded to top layer 14 by an adhesive 18. Layer 14 is shown comprised of inner hydrophilic layer 17 and outer, or external layer 15 of porous, expanded polytetrafluoroethylene.

EXAMPLE

A composite laminate according to the invention was made by the following procedure. Dilutions of Zelec ® DP, marketed by DuPont, of 5.0%, 2.5% and 1.0% were made. A fabric of Nomex ® polyamide fibers was first bonded to a two-layer sheet of expanded, porous polytetrafluoroethylene and hydrophilic layer as described in U.S. Pat. No. 4,194,041 with the porous expanded polytetrafluoroethylene layer oriented externally, using an adhesive as described in U.S. Pat. No. 4,532,316 and containing Antiblaze ® 100, marketed by Albright Wilson, Inc. The dilutions of antistatic agent described above were padded into three specimens of this Nomex ® fabric, partially air dried and then heated to 140° C. in a convection oven. These samples were then laminated on the Nomex ® side to a second 2-component layer of expanded, porous polytetrafluoroethylene and a hydrophilic layer as described above, again with the adhesive between the inner and outer layers. In this example, the expanded, porous polytetrafluoroethylene formed the external surfaces of the composite.

The specimens were tested by the NFPA 99 Static Decay Test, which measures the time of decay from a charge of 5000 volts to 500 volts, in seconds. Results are shown in Table 1.

TABLE 1

| Sample 1 | % Zelec DP | Dry Pick-Up of Antistat, Wt. % of Middle and Top Layers | Time of Decay of Laminate, sec. |
| --- | --- | --- | --- |
| 1 | 5% | 0.39 | .08–.09 |
| 2 | 2.5% | 0.17 | .12–.32 |
| 3 | 1% | 0.04 | 1.90–2.53 |
| 4 (Control) | 0% | 0 | >20 |

A flammability test was performed on the same samples as above according to Federal Test standard number 191A, Method 5903. Results are shown in Table 2.

TABLE 2

| Sample 2 | After flame, seconds | After glow, seconds | Charred length, inches |
| --- | --- | --- | --- |
| 1 | 0 | 0.9 | 2.6 |
| 2 | 0 | 1.4 | 1.6 |
| 3 | 0 | 1.5 | 1.9 |
| 4 (Control) | 0 | 1.6 | 1.9 |

While the invention has been disclosed herein in connection with certain embodiments and detailed descriptions, it will be clear to one skilled in the art that modifications or variations of such details can be made without deviating from the gist of this invention, and such modifications or variations are considered to be within the scope of the claims hereinbelow.

What is claimed is:

1. A flexible, breathable, antistatic, non-flammable, filtering, nonlinting, clean and cleanable composite laminate comprising:

(a) a middle layer of a non-flammable fabric containing an antistatic agent, and (b) a top and bottom layer each containing a sheet of porous, expanded polytetrafluoroethylene, said top and bottom layers being bonded to said middle layer by means of an adhesive between said middle layer and said top and bottom layers, wherein said porous, expanded polytetrafluroethylene sheets form the external surfaces of said composite laminate.

2. The composite of claim 1 wherein said top and bottom layer each comprise:

(a) a flexible, first layer of hydrophobic material having a moisture vapor transmission rate exceeding 1000 gms./m² · day and an advancing water contact angle exceeding 90 degrees, and (b) a continuous hydrophilic layer attached to the first layer, said hydrophilic layer having a moisture vapor transmission rate exceeding 1000 gms./m² · day and forming a barrier to passage of liquids with low surface tension.

3. The composite of claim 1 wherein said middle layer is a polyamide.

4. The composite of claim 3 wherein said middle layer is a woven polyamide fabric.

5. The composite of claim 3 wherein said middle layer is a knitted polyamide fabric.

6. The composite of claim 3 wherein said middle layer is a non-woven polyamide fabric.

7. The composite of claim 1 wherein said middle layer is a glass cloth.

8. The composite of claim 1 wherein said middle layer is a glass mat.

9. The composite of claim 1 wherein said antistatic agent is a dispersion of cationic polymers.

10. The composite of claim 1 wherein said antistatic agent is an electrically conducting filament.

11. The composite of claim 1 wherein said adhesive is a reactive polyurethane prepolymer comprising the reaction product of:

(i) a polyol (A) having a number average molecular weight of from 600 to 3500 and having a functionality of at least 2;

(ii) an isocyanate (B) having a functionality of at least 2; and (iii) a low molecular weight chain extender (C) having a molecular weight lower than 500 and having a functionality of at least 2, wherein the reactants are employed in such proportions so as to satisfy the following equations:

(a) $\dfrac{Eq_{NCO}}{Eq_{OH} + Eq_{CE}} \geq 1.1$ (b) $Eq_{OH} \geq Eq_{CE}$ (c) $Eq_{CE} > 0$, wherein $Eq_{NCO}$ denotes the equivalents of the isocyanate species employed, and $Eq_{OH}$ and $Eq_{CE}$ denote the respective molar equivalents of the polyol and chain extender employed, characterized in that said reactants are selected such that the reaction product of the isocyanate and chain extender provides suitable hard segments and soft segments and wherein said suitable hard segments are thermodynamically incompatible with said soft segments, the latter provided by the polyol, whereby phase separation of hard and soft segments in said prepolymer occurs at room temperature and renders said prepolymer a 100% solids, storage stable, segmented polyurethane prepolymer being an opaque solid at room temperature, said prepolymer having storage stability exceeding one month and being melt processible at room temperature below what would be considered to be the hard segment melt temperature.

* * * * *